United States Patent
Abdelghani

(10) Patent No.: US 10,611,703 B2
(45) Date of Patent: Apr. 7, 2020

(54) METHODS AND SYSTEMS FOR RECOVERING DICYCLOPENTADIENE FROM PYGAS

(71) Applicant: SABIC Global Technologies B.V., Bergen op Zoom (NL)

(72) Inventor: Mohamed Sabri Abdelghani, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 14 days.

(21) Appl. No.: 16/060,590

(22) PCT Filed: Dec. 6, 2016

(86) PCT No.: PCT/IB2016/057388
§ 371 (c)(1),
(2) Date: Jun. 8, 2018

(87) PCT Pub. No.: WO2017/103736
PCT Pub. Date: Jun. 22, 2017

(65) Prior Publication Data
US 2019/0225560 A1   Jul. 25, 2019

Related U.S. Application Data

(60) Provisional application No. 62/266,932, filed on Dec. 14, 2015.

(51) Int. Cl.
*C07C 2/50* (2006.01)
*C07C 4/22* (2006.01)
(Continued)

(52) U.S. Cl.
CPC ............ *C07C 2/50* (2013.01); *B01D 3/009* (2013.01); *C07C 4/22* (2013.01); *C07C 5/03* (2013.01);
(Continued)

(58) Field of Classification Search
None
See application file for complete search history.

(56) References Cited

U.S. PATENT DOCUMENTS 2,753,382 A * 7/1956 Hamner ............... C08F 36/04
585/17
3,436,437 A * 4/1969 Asaka ................. C07C 7/005
203/43
(Continued)

FOREIGN PATENT DOCUMENTS

JP       S5764622 A    4/1982
JP       S62889 B2     1/1987
(Continued)

OTHER PUBLICATIONS

Li et al. "Gas Phase Cracking of Dicyclopentadiene to Produce Cyclopentadiene." *Petroleum Science and Technology*, 31:1346-1352 (May 29, 2013).
(Continued)

*Primary Examiner* — Tam M Nguyen
(74) *Attorney, Agent, or Firm* — Norton Rose Fulbright US LLP

(57) ABSTRACT

Methods and systems for recovering dicyclopentadiene from pygas are provided. Methods can include heating pygas to generated heated pygas, recovering a $C_5$ fraction from the heated pygas, and dimerizing cyclopentadiene from the $C_5$ fraction to form dicyclopentadiene. Methods can further include recovering the $C_5$ fraction from the pygas in a depentanizer column. Other methods can include heating pygas including dicyclopentadiene to form cyclopentadiene and hydrogenating cyclopentadiene in the pygas to form cyclopentane.

12 Claims, 4 Drawing Sheets

(51) Int. Cl.
*C07C 5/03* (2006.01)
*B01D 3/00* (2006.01)
*C07C 7/04* (2006.01)
C07C 13/10 (2006.01)
C07C 13/15 (2006.01)
C07C 13/61 (2006.01)

(52) U.S. Cl.
CPC ............... *C07C 7/04* (2013.01); *C07C 13/10* (2013.01); *C07C 13/15* (2013.01); *C07C 13/61* (2013.01); *C07C 2601/08* (2017.05); *C07C 2601/10* (2017.05); *C07C 2603/68* (2017.05)

(56) References Cited

U.S. PATENT DOCUMENTS

| | | | | |
|---|---|---|---|---|
| 3,544,644 | A | 12/1970 | Robota | 260/666 |
| 3,598,877 | A * | 8/1971 | Fountain et al. | C07C 4/22 585/256 |
| 3,674,883 | A * | 7/1972 | Schleppinghoff | C07C 7/005 585/362 |
| 3,676,509 | A | 7/1972 | Helman | 260/666 PY |
| 3,705,204 | A * | 12/1972 | Horie et al. | C07C 7/005 585/255 |
| 3,719,718 | A | 3/1973 | Grude et al. | 260/666 A |
| 3,788,979 | A * | 1/1974 | Caflisch et al. | C10G 69/06 208/255 |
| 3,947,506 | A * | 3/1976 | Lybarger | C07C 7/005 585/259 |
| 5,321,177 | A * | 6/1994 | Nakamura | C07C 4/22 203/30 |
| 5,378,783 | A * | 1/1995 | Okumura | C07C 7/14833 203/6 |
| 5,877,366 | A | 3/1999 | Birmingham | 585/354 |
| 6,737,557 | B2 | 5/2004 | Cheung et al. | 585/809 |
| 2008/0097132 | A1 | 4/2008 | Prindle, Jr. et al. | 585/354 |
| 2009/0112033 | A1* | 4/2009 | Hosotani | C07C 13/605 585/361 |
| 2011/0178349 | A1 | 7/2011 | Anzick et al. | 585/318 |
| 2014/0364665 | A1* | 12/2014 | Ramanujam | C07C 7/005 585/361 |

FOREIGN PATENT DOCUMENTS

JP 2004323485 11/2004
WO WO2002036529 A1 5/2002

OTHER PUBLICATIONS

Search Report and Written Opinion from PCT/IB2016/057388, dated Apr. 5, 2017, 11 pages.

* cited by examiner

METHODS AND SYSTEMS FOR RECOVERING DICYCLOPENTADIENE FROM PYGAS

CROSS-REFERENCE TO RELATED APPLICATIONS

This application is a national phase application under 35 U.S.C. § 371 of International Application No. PCT/IB2016/057388 filed Dec. 6, 2016, which claims priority to U.S. Provisional Patent Application No. 62/266,932 filed Dec. 14, 2015. The entire contents of each of the above-referenced disclosures is specifically incorporated by reference herein without disclaimer.

FIELD

The disclosed subject matter relates to methods and systems for recovering dicyclopentadiene from pygas.

BACKGROUND

Pygas, also known as pyrolysis gas, can be formed in the cracking furnaces of various refinery processes. Pygas can include alkanes, alkenes, alkynes, aromatics, naphthenes, alkyl aromatics and/or polyaromatics. After being formed in the cracking furnaces, pygas can be distilled through one or more fractional distillation columns to remove lighter hydrocarbons.

One potentially valuable component of pygas is dicylcopentadiene. Dicyclopentadiene can be formed by the thermal dimerization of cyclopentadiene in pygas. Thermal dimerization of cyclopentadiene to dicyclopentadiene can occur as the lighter hydrocarbons are distilled from pygas. However, because pygas components can have similar vapor pressures, i.e., low relative volatilities, it can be difficult to remove dicyclopentadiene from the heavier hydrocarbons in pygas by distillation alone. As a result, dicyclopentadiene can be used as fuel, e.g., for boilers and furnaces, along with heavier hydrocarbons. However, it can be more desirable to recover purified dicyclopentadiene from pygas.

Certain methods of recovering dicyclopentadiene from pygas are known in the art. For example, U.S. Pat. No. 6,737,557 discloses a method for recovering dicyclopentadiene from a hydrocarbon feedstock using two distillation columns. U.S. Patent Publication No. 2014/0364665 discloses a system including a distillation column and at least two dimerization reactors. U.S. Pat. No. 3,719,718 discloses a process that includes monomerizing dicyclopentadiene to form cyclopentadiene. U.S. Pat. No. 3,676,509 discloses a method for recovering dicyclopentadiene from a hydrocarbon feedstock by monomerizing dicyclopentadiene at temperatures from about 350° C. to about 420° C. International Patent Publication No. WO2002/036529 discloses a process for purifying dicyclopentadiene from a $C_5$ fraction which includes the conversion of cyclopentadiene to dicyclopentadiene prior to separating dicyclopentadiene from the $C_5$ fraction.

Japanese Patent No. 62000889B2 discloses the production of cyclopentadiene through the pyrolysis of dicyclopentadiene. U.S. Pat. No. 3,544,644 discloses liquid phase cracking of dicyclopentadiene to form cyclopentadiene. U.S. Pat. No. 5,877,366 discloses cracking dicyclopentadiene using a heat transfer fluid to form cyclopentadiene vapor. U.S. Patent Publication No. 2008/0097132 discloses a process of forming cyclopentadiene from cyclopentenes, including dicyclopentadiene, by heating the cyclopentenes in a vaporization zone prior to transfer to a cracking zone.

However, there remains a need for improved techniques for recovering dicyclopentadiene from pygas.

SUMMARY OF THE DISCLOSED SUBJECT MATTER

The disclosed subject matter provides methods and systems for recovering dicyclopentadiene from pygas.

In certain embodiments, an exemplary method for recovering dicyclopentadiene from pygas includes heating pygas to form heated pygas, recovering a $C_5$ fraction from the heated pygas, and dimerizing cyclopentadiene from the $C_5$ fraction to form dicyclopentadiene. In certain embodiments, the method can further include separating $C_1$ through $C_4$ hydrocarbons from the pygas prior to heating the pygas.

In certain embodiments, the pygas can be heated in a thermal reactor for about 1 to about 3 hours at a temperature of about 170° C. to about 190° C. and at a pressure of about 13 to about 16 bar. In certain embodiments, dicyclopentadiene in the pygas can be monomerized to cyclopentadiene. In certain embodiments, the $C_5$ fraction can be recovered from the pygas by distilling a $C_5$ stream in a depentanizer column. In accordance with the disclosed subject matter, the amount of recovered dicyclopentadiene can be increased as compared to an amount recovered from a non-heated pygas stream with the same initial dicyclopentadiene content.

In certain embodiments, an exemplary method includes feeding a stream including pygas to a depentanizer column with a bottom column temperature of about 170° C. to about 190° C., recovering a $C_5$ fraction from the pygas, and dimerizing cyclopentadiene from the $C_5$ fraction to form dicyclopentadiene.

In certain embodiments, an exemplary method for producing cyclopentane from pygas containing dicyclopentadiene includes heating the pygas to form cyclopentadiene, and hydrogenating the cyclopentadiene to form cyclopentane.

The presently disclosed subject matter also provides systems for recovering dicyclopentadiene from pygas. An exemplary system can include a first thermal reactor for converting the dicyclopentadiene in the pygas stream to cyclopentadiene and a depentanizer column, coupled to the first thermal reactor, for separating a $C_5$ fraction including cyclopentadiene from the pygas.

In certain embodiments, the system can further include one or more distillation columns coupled to the first thermal reactor for separating $C_1$ through $C_4$ hydrocarbons from the pygas. The system can further include a second thermal reactor coupled to the depentanizer column for converting cyclopentadiene in the $C_5$ fraction to dicyclopentadiene and a distillation column for removing dicyclopentadiene from the $C_5$ fraction.

In certain embodiments, an exemplary system for producing cyclopentane from pygas containing dicyclopentadiene can include a first thermal reactor for converting the dicyclopentadiene in the pygas to cyclopentadiene and a hydrogenation reactor coupled to the first thermal reactor for converting the cyclopentadiene to cyclopentane. The system can further include a recycle line for transferring cyclopentane.

DETAILED DESCRIPTION

The presently disclosed subject matter provides methods and systems for recovering dicyclopentadiene from pygas.

Figure 1:
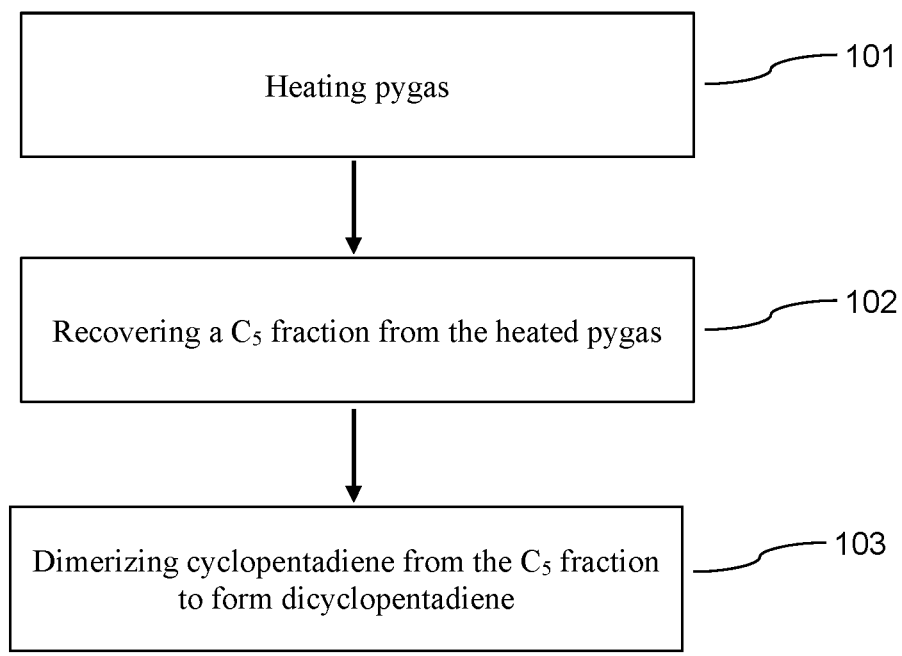
FIG. 1 depicts a method for recovering dicyclopentadiene from pygas according to one exemplary embodiment of the disclosed subject matter.

The presently disclosed subject matter provides methods for recovering dicyclopentadiene from pygas. For the purpose of illustration and not limitation, FIG. 1 is a schematic representation of an exemplary method according to a non-limiting embodiment of the disclosed subject matter.

In certain embodiments, a method 100 for recovering dicyclopentadiene from pygas includes heating pygas to generate heated pygas. The pygas of the presently disclosed subject matter can originate from various sources, for example other chemical processes, e.g., ethylene production or the cracking of naphtha, butanes, or gas oil. The pygas can include alkanes, alkenes, alkynes, aromatics, naphthenes, alkyl aromatics, and polyaromatics. For example, the pygas can include cyclopentadiene and/or dicyclopentadiene. In certain embodiments, prior to heating, the pygas can include from about 0.1 wt-% to about 50 wt-% cyclopentadiene and from about 0.1 wt-% to about 50 wt-% dicyclopentadiene.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In certain embodiments, the method can further include preprocessing the pygas prior to heating. For example, $C_1$ through $C_4$ hydrocarbons can be removed from the pygas, e.g., in a demethanizer, deethanizer, depropanizer, and/or debutanizer. In certain embodiments, the pygas is preprocessed such that it contains only $C_5$ and heavier hydrocarbons.

In certain embodiments, the pygas can be heated at a temperature from about 130° C. to about 230° C., from about 150° C. to about 210° C., or from about 170° C. to about 190° C. The pygas can be heated for a time period from about 30 minutes to about 5 hours, or from about 1 hour to about 3 hours. The pygas can be heated at a pressure from about 5 bar to 25 bar, 10 bar to about 20 bar, or from about 13 bar to about 16 bar. The pygas can be heated in the liquid phase. In certain embodiments, the pygas can be heated in a thermal reactor.

In certain embodiments, the method can further include converting dicyclopentadiene in the pygas to cyclopentadiene by heating the pygas. For example, the amount of dicyclopentadiene in the pygas that is converted to cyclopentadiene can be greater than 50%, greater than 60%, greater than 70%, greater than 80%, or greater than 90%.

In certain embodiments, the method 100 can further include recovering a $C_5$ fraction from the heated pygas 102. The $C_5$ fraction can include aliphatic and aromatic hydrocarbons, e.g., pentanes, pentenes, pentynes, cyclopentanes, cyclopentenes, and/or cyclopentadiene. For example, the $C_5$ fraction can contain from about 1 wt-% to about 80 wt-% cyclopentadiene.

In certain embodiments, the $C_5$ fraction can be recovered from the heated pygas by distillation, i.e., in a fractional distillation column. In particular embodiments, both heating the pygas and recovering a $C_5$ fraction from the heated pygas can be performed in a single distillation column. The distillation column can be a depentanizer column.

In certain embodiments, the method 100 further includes dimerizing cyclopentadiene from the $C_5$ fraction to form dicyclopentadiene 103. The cyclopentadiene can be dimerized by thermal dimerization. In certain embodiments, the cyclopentadiene is dimerized at a temperature of less than about 180° C., less than to about 170° C., or less than about 160° C. After dimerization, the $C_5$ fraction can contain from about 1 wt-% to about 80 wt-% dicyclopentadiene.

In certain embodiments, the method can further include separating dicyclopentadiene from the $C_5$ fraction. The dicyclopentadiene can be separated by fractional distillation, e.g., in a distillation column, to produce a dicyclopentadiene stream.

In accordance with the disclosed subject matter, the amount of dicyclopentadiene recovered from the pygas is increased as compared to an amount recovered from a non-heated pygas stream with the same initial dicyclopentadiene content. In certain embodiments, greater than about 80%, greater than about 85%, or greater than about 90% of dicyclopentadiene is recovered from the pygas. The dicyclopentadiene recovered in accordance with the disclosed subject matter can have high purity, for example, the dicyclopentadiene stream can contain greater than about 85 wt-%, greater than about 90 wt-%, or greater than about 95 wt-% dicyclopentadiene.

Figure 2:
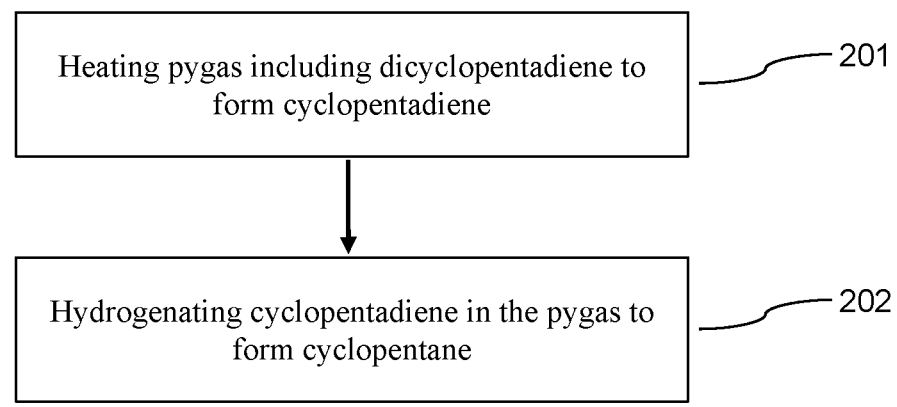
FIG. 2 depicts a method for producing cyclopentane from pygas containing dicyclopentadiene according to another exemplary embodiment of the disclosed subject matter.

In certain embodiments, dicyclopentadiene can be recovered from the pygas and converted to cyclopentane. For the purpose of illustration and not limitation, FIG. 2 provides a schematic representation of a method for producing cyclopentane from pygas containing dicyclopentadiene according to another non-limiting embodiment of the disclosed subject matter. The method 200 includes heating pygas containing dicyclopentadiene to form cyclopentadiene 201. The pygas can be heated according to the methods discussed above.

The method 200 further includes hydrogenating cyclopentadiene in the pygas to form cyclopentane 202. In certain embodiments, a $C_5$ fraction including cyclopentadiene can be separated from the pygas, and the $C_5$ fraction can be hydrogenated. In certain embodiments, cyclopentane produced by the hydrogenation reaction can be recycled to another chemical process, e.g., naphtha cracking.

Figure 3:
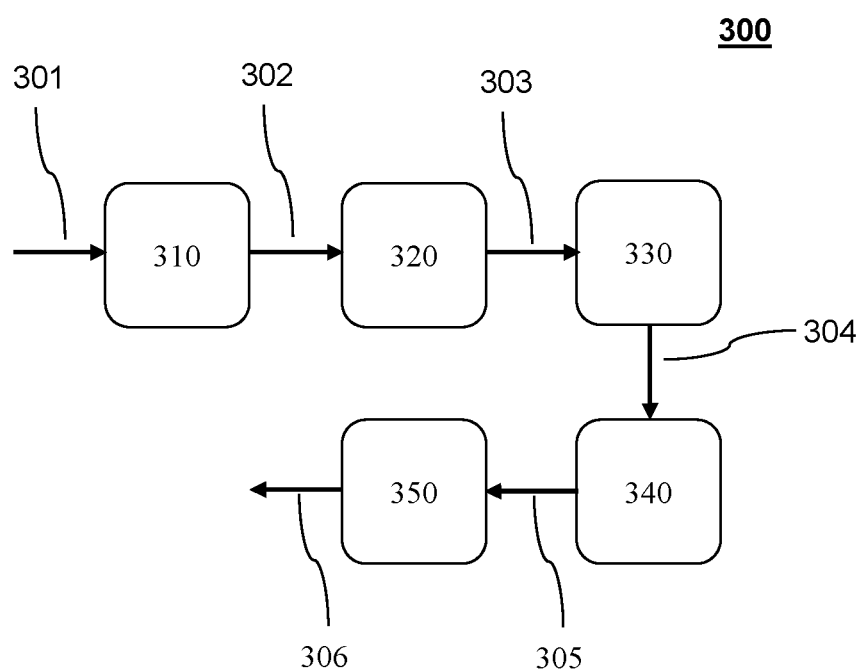
FIG. 3 depicts a system for recovering dicyclopentadiene from pygas according to one exemplary embodiment of the disclosed subject matter.

The presently disclosed subject matter further provides systems for recovering dicyclopentadiene from pygas. The system can include one or more thermal reactors and one or more distillation columns. For the purpose of illustration and not limitation, FIG. 3 is a schematic representation of an exemplary system according to a non-limiting embodiment of the disclosed subject matter.

In certain embodiments, a system 300 for recovering dicyclopentadiene from pygas includes a feed line 302 coupled to a first thermal reactor 320 for transferring pygas to the first thermal reactor. The first thermal reactor can be adapted to heat the pygas and monomerize dicyclopentadiene to cyclopentadiene. The first thermal reactor can be any type known in the art to be suitable for the monomerization of dicyclopentadiene to cyclopentadiene. The first thermal reactor can include one or more heat sources. The first thermal reactor can be made of any suitable material including, but not limited to, aluminum, stainless steel, carbon steel, glass-lined materials, polymer-based materials, nickel-base metal alloys, cobalt-based metal alloys or combinations thereof.

"Coupled" as used herein refers to the connection of a system component to another system component by any applicable means known in the art. The type of coupling used to connect two or more system components can depend on the scale and operability of the system. For example, and not by way of limitation, coupling of two or more components of a system can include one or more joints, valves, transfer lines or sealing elements. Non-limiting examples of joints include threaded joints, soldered joints, welded joints, compression joints and mechanical joints. Non-limiting examples of fittings include coupling fittings, reducing coupling fittings, union fittings, tee fittings, cross fittings and flange fittings. Non-limiting examples of valves include gate valves, globe valves, ball valves, butterfly valves and check valves.

In certain embodiments, the feed line 302 can also be coupled to one or more distillation columns 310 for removing $C_1$ through $C_4$ hydrocarbons from the pygas. The one or more distillation columns can be upstream from the first thermal reactor. The distillation columns for use in the presently disclosed subject matter can be any type known in the art to be suitable for fractional distillation. In certain embodiments, the one or more distillation columns can be a demethanizer, deethanizer, depropanizer and/or debutanizer. The one or more distillation columns can be adapted to continuous or batch distillation. The one or more distillation columns can be coupled to one or more condensers and one or more reboilers. The one or more distillation columns can be stage or packed columns, and can include plates, trays and/or packing material. The one or more distillation columns can be coupled to one or more transfer lines. The one or more distillation columns can be made of any suitable material including, but not limited to, aluminum, stainless steel, carbon steel, glass-lined materials, polymer-based materials, nickel-base metal alloys, cobalt-based metal alloys or combinations thereof.

In certain embodiments, the first thermal reactor 320 can be further coupled to a depentanizer column 330. The depentanizer column can be a distillation column. The depentanizer column can be adapted to separate a stream containing a $C_5$ fraction from a stream containing $C_6$ and heavier hydrocarbons. The depentanizer column can be coupled to one or more transfer lines 304 for removing the stream containing a $C_5$ fraction from the depentanizer column.

In particular embodiments, the depentanizer column 330 is not coupled to a first thermal reactor and is directly coupled to the feed line containing pygas 302. The depentanizer column can be adapted to heat the pygas to temperatures from about 130° C. to about 230° C., from about 150° C. to about 210° C., or from about 170° C. to about 190° C. The bottom of the depentanizer column can be sized such that the pygas has a residence time in the bottom of the column sufficient for the dicyclopentadiene to monomerize to cyclopentadiene. For example, the residence time in the bottom of the column can be from about 30 minutes to about 5 hours, or from about 1 hour to about 3 hours.

In certain embodiments, the depentanizer column 330 can be coupled to a second thermal reactor 340, e.g., via one or more transfer lines 304 for transferring a $C_5$ fraction containing cyclopentadiene to the second thermal reactor. The second thermal reactor can be any type known in the art to be suitable for the dimerization of cyclopentadiene to dicyclopentadiene. The second thermal reactor can include one or more heat sources. The second thermal reactor can be made of any suitable material including, but not limited to, aluminum, stainless steel, carbon steel, glass-lined materials, polymer-based materials, nickel-base metal alloys, cobalt-based metal alloys or combinations thereof.

In certain embodiments, the second thermal reactor 340 can be coupled to one or more distillation columns 350, e.g., via one or more transfer lines 305 for transferring a $C_5$ fraction containing dicyclopentadiene to the one or more distillation columns. The one or more distillation columns can be adapted to separate dicyclopentadiene from the $C_5$ fraction.

Figure 4:
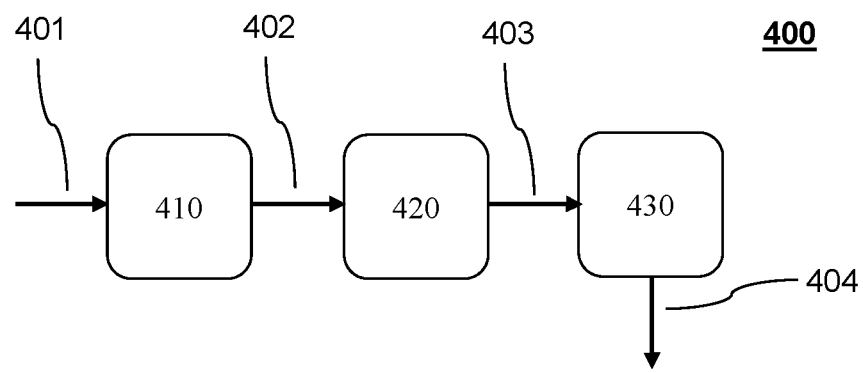
FIG. 4 depicts a system for producing cyclopentane from pygas containing dicyclopentadiene according to another exemplary embodiment of the disclosed subject matter.

For the purpose of illustration and not limitation, FIG. 4 provides a schematic representation of a system for producing cyclopentane from pygas containing dicyclopentadiene according to another non-limiting embodiment of the disclosed subject matter. In certain embodiments, the system 400 can include a hydrogenation reactor 430 for converting cyclopentadiene to cyclopentane. The hydrogenation reactor can be coupled to either of the first thermal reactor 410 or the depentanizer column 420, e.g., via one or more transfer lines 402, 403. The hydrogenation reactor can be any reactor type suitable for the hydrogenation of cyclopentadiene to form cyclopentane. By way of example, but not limitation, such reactors include fixed bed reactors, such as tubular fixed bed reactors and multi-tubular fixed bed reactors, fluidized bed reactors, such as entrained fluidized bed reactors and fixed fluidized bed reactors, and slurry bed reactors such as three-phase slurry bubble columns and ebullated bed reactors.

In certain embodiments, the system 400 can include a recycle line 404 coupled to the hydrogenation reactor for transferring cyclopentane to a cracking process, e.g., ethylene production or the cracking of naphtha.

The presently disclosed systems can further include additional components and accessories including, but not limited to, one or more gas exhaust lines, cyclones, product discharge lines, reaction zones, heating elements and one or more measurement accessories. The one or more measurement accessories can be any suitable measurement accessory known to one of ordinary skill in the art including, but not limited to, pH meters, flow monitors, pressure indicators, pressure transmitters, thermowells, temperature-indicating controllers, gas detectors, analyzers and viscometers. The components and accessories can be placed at various locations within the system.

The methods and systems of the presently disclosed subject matter provide advantages over certain existing technologies. Exemplary advantages include integration with existing chemical processes, increased recovery of dicyclopentadiene from pygas, and improved purity of dicyclopentadiene product.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of recovering dicyclopentadiene from pygas, the method comprising:
    (a) heating the pygas to generate heated pygas;
    (b) recovering a $C_5$ fraction from the heated pygas; and
    (c) dimerizing cyclopentadiene from the $C_5$ fraction to form dicyclopentadiene;
wherein the heating comprises heating the pygas in a thermal reactor for about 1 to about 3 hours at a temperature of about 170° C. to about 190° C.; and
wherein the heating further comprises heating the pygas at a pressure of about 13 to about 16 bar.

2. The method of claim 1, further comprising separating C1 through C4 hydrocarbons, if any, from the pygas prior to the heating.

3. The method of claim 1, wherein the heating comprises heating the pygas in a thermal reactor for about 1 to about 3 hours at a temperature of about 170° C.

4. The method of claim 3, wherein the heating further comprises heating the pygas at a pressure of about 13 bar.

5. The method of claim 1, wherein the dicyclopentadiene is monomerized to cyclopentadiene.

6. The method of claim 1, wherein the recovering comprises distilling a C5 stream in a depentanizer column.

7. The method of claim 1, wherein the heating comprises feeding a stream comprising the pygas to a depentanizer column with a bottom column temperature of about 170° C. to about 190° C.

8. A method of producing cyclopentane from pygas comprising dicyclopentadiene, the method comprising:
    (a) heating the pygas to form cyclopentadiene in a thermal reactor for about 1 to about 3 hours at a temperature of about 170° C. to about 190° C. at a pressure of about 13 to about 16 bar; and
    (b) hydrogenating the cyclopentadiene to form cyclopentane.

9. The method of claim 1, wherein the dicyclopentadiene is monomerized to cyclopentadiene and wherein the recovering comprises distilling a C5 stream in a depentanizer column.

10. The method of claim 1, wherein the dicyclopentadiene is monomerized to cyclopentadiene, and wherein the heating comprises feeding a stream comprising the pygas to a depentanizer column with a bottom column temperature of about 170° C. to about 190° C.

11. The method of claim 1, wherein the dicyclopentadiene is monomerized to cyclopentadiene, wherein the heating comprises feeding a stream comprising the pygas to a depentanizer column with a bottom column temperature of about 170° C. to about 190° C., and wherein the recovering comprises distilling a C5 stream in a depentanizer column.

12. The method of claim 1, wherein the heating comprises feeding a stream comprising the pygas to a depentanizer column with a bottom column temperature of about 170° C. to about 190° C.

* * * * *